United States Patent [19]

Scheicher et al.

[11] Patent Number: 4,917,702
[45] Date of Patent: Apr. 17, 1990

[54] BONE REPLACEMENT MATERIAL ON THE BASIS OF CARBONATE AND ALKALI CONTAINING CALCIUMPHOSPHATE APATITES

[76] Inventors: Hans Scheicher, Rondell Neuwittelsbach 4, 8000 München 19; Eberhard Wendler, Sedelhofstr. 3, 8000 München 60, both of Fed. Rep. of Germany

[21] Appl. No.: 153,885

[22] Filed: Feb. 9, 1988

Related U.S. Application Data

[63] Continuation-in-part of Ser. No. 866,199, May 9, 1986, abandoned.

[30] Foreign Application Priority Data

Sep. 10, 1984 [DE] Fed. Rep. of Germany ....... 3433210

[51] Int. Cl.$^4$ ..................... A61F 2/28; C04B 35/00; A61C 13/08
[52] U.S. Cl. ..................................... 623/16; 501/1; 501/151; 433/212.1
[58] Field of Search ..................... 623/16; 501/1, 151; 433/201.1, 212.1; 106/35

[56] References Cited

U.S. PATENT DOCUMENTS

3,922,155  11/1975  Broemer et al. .
3,929,971  12/1975  Roy .
3,981,736  9/1976  Broemer et al. .
4,222,128  9/1980  Tomonaga et al. .
4,373,217  2/1983  Draenert .
4,429,691  2/1984  Niwa et al. .
4,497,075  2/1985  Niwa et al. .
4,503,157  3/1985  Hatahira .

FOREIGN PATENT DOCUMENTS

1195615  10/1985  Canada .
0120689  10/1984  European Pat. Off. .

OTHER PUBLICATIONS

F. C. M. Driessens, *Bioceramics of Calcium Phosphate*, 1983.
LeGeros et al., Science, vol. 155, pp. 1409-1411, Mar. 17, 1967.

Primary Examiner—Alan W. Cannon
Attorney, Agent, or Firm—Millen, White & Zelano

[57] ABSTRACT

This invention sets forth an agent for filling bone and tooth defects, for building up bone, for bone-contact layers and for the replacement of bones and the roots of teeth, which contains calcium phosphate apatite having carbonate and alkali portions, all ions being definedly integrated in the crystal lattice; use is optionally made together with additives and/or diluents both tolerated by the body. Furthermore, it sets forth the use of this apatite for filling bone and tooth defects, for building up bone, for bone-contact layers, as a replacement for bones and the roots of teeth and as an implant article consisting completely or partially of this apatite or consisting of a material known for implant articles and being coated completely or partially with a layer of this apatite.

25 Claims, 5 Drawing Sheets

BONE REPLACEMENT MATERIAL ON THE BASIS OF CARBONATE AND ALKALI CONTAINING CALCIUMPHOSPHATE APATITES

This application is a continuation-in-part of parent application Ser. No. 866,199, filed May 9, 1986 (now abandoned).

BACKGROUND OF THE INVENTION

This invention relates to a bone replacement material on the basis of calcium phosphate apatites having carbonate and alkali portions, all ions being definedly integrated in the crystal lattice, for the filling of bone defects, for building up bones, for bone-contact layers on replacements of bones and roots of teeth and for independent smaller bone replacement parts and implants, as well as the production and processing thereof.

Hereinafter, the material according to this invention is referred to as $MeCO_3$ apatite for reasons of simplification; Me stands for metal ions, $CO_3$ stands for carbonate ions, apatite stands for calcium phosphate apatite.

Owing to the rapid development of surgery, it is nowadays possible to carry out operations to bones and joints which were still inconceivable a little while ago. For example, it is now possible to carry out surgical removal of cysts, foci of suppuration in bone and malignant tumors from bones. This results in defects in the bone, which need to be filled since normal bone repair processes are no longer able to compensate them. Some defects of this type may have a volume of up to 600 $cm^3$ which has to be filled again. Cavities are also produced during the treatment of teeth, which have to be filled again.

For filling cavities of this type use is made of bone replacement materials in liquid, pasty or solid form as granules or articles for implantation. If the cavities which are to be filled are not too large then the purpose of the bone replacement materials is to temporarily fill the cavities in the bone and to allow the body itself to compensate, in the course of time, the defect with living bone material. This may entail there being either growth around the replacement material, which stays in place without irritation, or slow breakdown and replacement thereof by living bone.

It is necessary to use a material which is compatible with bone for filling larger cavities with bone replacement material. The materials of this type which are used are endogenous or exogenous fragments of bone or hydroxyapatite granules. Only very limited amounts of endogenous bone material are available, and additional surgical operations are necessary to obtain it. It is necessary to remove all antigens from exogenous, for example animal, bone materials in order to avoid rejection reactions, but this is only partially successful in practice.

When hydroxyapatite is used there is primarily irritation of the surrounding bone material. Thus, there is a need for a material which can be used in liquid, pasty or solid form for filling cavities in bones, that is to say for filling bone defects and which does not cause any primary irritations.

Bone implants are frequently used in surgical operations. Bone implants are items which are implanted in the bones of the body of a recipient and permanently replace parts of the skeleton or roots of teeth. The outer layer of the bone implant, which comes into contact with the living substrate bone, is termed the bone-contact layer. At the present time, metals, such as, for example, special steels, noble metals, titanium, ceramic materials, such as, for example, alumina, glass-ceramics, hydroxy-apatite ceramics and synthetic materials are used as bone implants and as bone-contact layers.

These substances are classified as biocompatible and bioactive according to the tissue compatibility. Biocompatible substances are tolerated by the body in the long term without rejection. Bioactive substances become rigidly incorporated like endogenous tissue, the tissue compatibility being determined by the chemical composition, the crystalline structure, the surface structure and the mechanical properties.

The metals and some ceramic materials, such as, for example, alumina ceramics, are biocompatible. Ensheathing by connective tissue always takes place in the body. This connective tissue layer allows the implant to be held relatively rigidly, but does not allow frictional connection to the mineral framework of the substrate bone.

Because of the absence of primary integration into the substrate bone, a biocompatible implant of this type can be exposed to only slight mechanical stress since otherwise it is held increasingly poorly, and this is associated with pain and, finally, the loss of the implant. This is found, for example, with hipjoint prostheses, which are always subject to great stress and for which nowadays more than one quarter of the operations are carried out because of loosening of an implant which had previously been inserted.

Thus, additional undercutting such as, for example, a screw thread is necessary for permanent mechanical anchoring of biocompatible implants in bone. With all metallic implants it is still an unanswered question of whether they release toxic metal ions into the surroundings and thus may have adverse effects in the long term.

Even when bone cement is used, despite the initially better mechanical connection to the substrate bone, a loosening which has been described takes place, with some delay.

In the case of bioactive materials, after some time the bone material grows directly thereon. Among the known materials, the best properties in this respect are shown by hydroxyapatite which, after a period, which lasts only a few weeks, of mild signs of irritation, which can be detected under the microscope by giant cells around the implant, is integrated into the substrate bone without an interlayer.

As a rule, bioactive materials are difficult to work and less mechanically stable than the biocompatible metals or ceramics.

Thus, there has been a change to the use of combined implants comprising biocompatible cores such as, for example, titanium, special steel and alumina, and bioactive surface coatings (compare German Patent Specification No. 2,840,064). A combined implant construction of this type may have considerable advantages since, in this case, high mechanical stability of complex-shaped implants is combined with rapid and rigid connection to the substrate bone. Again, signs of irritation appear after the insertion of implants of this type with the bioactive coatings hitherto known, but these signs subside after some time. Thus, there is a great need for a material which can be used for the production of implants or for the production of bone-contact layers for implants, and which has the necessary bioactive and biomechanical properties and enables osteointegration without irritation

SUMMARY OF THE INVENTION

The present invention has the object of making available an agent for the filling of bone defects, for building up bone, for the replacement of bone and the roots of teeth, and for bone-contact layers, which agent fuses rapidly and rigidly to the bone without, or with only extremely mild, signs of irritation.

The agent which is to be made available according to the invention is one which, when it is used as a filling for bone defects, for building up bone and for replacement of bone and the roots of teeth, results in no rejection reactions and is available in unlimited amounts. The agent is to grow in, without a period of irritation, and either replace the living bone or be replaced by living bone.

The agent which is to be made available according to the invention should make it possible to shorten the observed period of irritation and increase the rate of bone infiltration when it is used as a bone-contact layer, so that it is possible to insert bioactive implants with the highest possible rate of success for the patient. A considerable shortening of the settling-in period means that the patient can subject the corresponding parts of the body to mechanical stress at an earlier time, and thus diminish the operative risk.

The invention relates to an agent for the filling of bone and tooth defects, for building up bone, for bone-contact layers and for replacement of bone and the roots of teeth, which contains $MeCO_3$ apatite, where appropriate together with additives and/or diluents which are tolerated by the body.

The invention furthermore relates to the use of $MeCO_3$ apatite for the filling of bone and tooth defects, for building up bone, for bone-contact layers and as a replacement for bone and as a replacement for the roots of teeth.

The invention furthermore relates to an article for implantation which is composed entirely or partially of $MeCO_3$ apatite or is composed of a material known for articles for implantation and is coated entirely or partially with a layer of $MeCO_3$ apatite.

It has been found, surprisingly, that $MeCO_3$ apatite or $MeCO_3$ containing apatites undergo rigid bonding to the bone in the body without there being a lengthy period with signs of irritation. The properties of $MeCO_3$ apatites for the qrowing on of bone mineral in the body are better than those of hydroxyapatite. This is presumably attributable to their chemical properties and crystalline structures.

The investigations which have been carried out lead to the conclusion, although this is not intended to be a restriction to any particular theory, that the initial signs of irritation and the delayed incorporation of hydroxyapatite in bone may be interpreted as a chemical modification of the surface of the implant. In the carbonate and alkali containing milieu of the bone, the surface of the hydroxyapatite presumably undergoes carbonatization, that is to say conversion into carbonate and alkali containing apatite, before deposition of bone mineral on the implant can take place. This phase is omitted by the material according to the invention. Thus, an implant with a surface of $MeCO_3$ apatite can undergo more rapid and more rigid incorporation in the bone. The crystalline composition of bone apatite differs from that of hydroxyapatite. Hence epitaxic growing of bone mineral onto the implant, and thus also a rigid crystalline connection, is promoted when the implant itself offers $MeCO_3$ apatite crystals as a host lattice.

In animal experiments, in which implants with $MeCO_3$ apatite surfaces were inserted into the femur of rats, a rigid connection to the substrate bone was observed after only one week. This was surprising and had not been obvious. The rapid growing onto the implant is also of importance for the long-term success since even slight movements on subjection to mechanical stress result in sheathing of the implant with connective tissue, which permanently prevents direct growing on of bone material. Thus, a surface coating of the material according to the invention ensures that the implant can bear stress earlier and improve its prognosis compared with implants made of the materials hitherto customary.

According to this invention, a calcium phosphate apatite having defined carbonate and alkali portions is used, which is referred to as $MeCO_3$ apatite for the purpose of simplification. It is a complex calcium phosphate carbonate salt having a chemical structure analogous to that of hydroxyapatite. The calcium/phosphate ratio directly depends on the doping of the alkali and carbonate ions.

There is no consistency with the term apatite even in the scientific literature. For this reason, the chemical formulae of the unit cell of the crystal of various calcium phosphate apatites are detailed below:

I. Hydroxyapatite:
$Ca_{10}(PO_4)_6(OH)_2$

II. "Pure" carbonate apatite:
$Ca_{10-x}(PO_4)_{6-x}(CO_3)_x(OH)_{2-x}$

III. $MeCO_3$ apatite according to this invention:

$Me^{II}_a Me^{I}_b (PO_4)_{6-x}(CO_3)_x(OH)_{2-b-x}(H_2O)_w$ $MeCO_3$ containing apatite structure having the most frequent and most important foreign ions, Me representing metal ions. Of particular importance is $Na^+$ as a singly charged metal ion.

- a represents the number of doubly charged metal ions except for Ca and stands for a value from 0 to 1.0, preferably from 0 to 0.6;
- b represents the number of singly charged metal ions and stands for a value from 0 to 1.2, preferably from 0 to 1.0, particularly preferably from 0.05 to 0.5;
- x represents the number of carbonate ions and stands for a value from 0.2 to 1.2;
- w represents the number of the water molecules integrated in the crystal lattice and stands for a value from 0 to (b+x), the sum (b+x) being a maximum of 2.0.

Examples of singly charged, metal ions are: $Na^+$, $K^+$ and $Ag^+ \rightarrow Ca^{2+} + OH$ and also Examples of doubly charged metal ions are: $Mg^{2+}$, $Pb^{2+}$, $Sr^{2+}$, $Cd^{2+}$ and $Mn^{2+} \rightarrow Ca^{2+}$.

According to the invention, the apatite mentioned under item III is used and referred to as $MeCO_3$ apatite. It is used in the form of powders, granules, molded bodies or as a coating.

According to the invention, this apatite may contain the indicated ions compatible with its crystal structure in a combination to control its biological properties, these ions at those positions in the lattice given in the formula and within the quantity sum given being components of the crystal lattice. In exchange with OH ions, halide ions, e.g. fluorine, may optionally also be integrated in the crystal lattice.

It is possible to add additives and/or diluents, physiological saline solutions and/or medicaments and/or hormones all tolerated by the body to the $MeCO_3$ apatite according to the invention. The content of these substances each depends on the use; the person skilled in the art is familiar with the use of these substances.

All additives and diluents tolerated by the body may be used, as they are used already now in the fields mentioned.

Examples of organic binders are acrylates, such as polymethylmethacrylate bone cements, other polymerizable synthetic materials, such as polyesters, polysaccharides which are able to gel, such as agarose, gelatin, and crosslinking polypeptides, such as fibrin adhesive, autologous blood or serum of the patient.

Examples of inorganic binders are silicates, such as glasses, ceramic compositions, hydraulic binders, such as cements, and silicones.

Examples which may be mentioned of salt solutions are sodium chloride solution, Ringer's solution and bicarbonate solution. Examples of medicaments which may be mentioned are antibiotics, carnosine, heparin, hyaluronidase, colloidal silver or a silver salt. Also examples a of hormones which may be mentioned are anabolic steroids, calcitonin, parathyroid hormone and growth hormone (STH).

The exact admixtures to the agent according to the invention depend on the intended use and can readily be established by those skilled in the art.

For replacing parts of the skeleton and for bioactive coating of endoprostheses it is expedient to use a stoichiometrically pure hydroxyapatite masked with the $MeCO_3$ apatite according to this invention only on the surface, since, on the one hand, the $MeCO_3$ coated surface effects an osteointegration of the implant without causing irritation and, on the other hand, the hydroxyapatite core of the crystallites prevents resorption of the material.

For filling bone defects which result after operations of inflammable bone processes or after tumor operations, it is expedient to use a uniform $MeCO_3$ apatite material according to this invention, since this material is incorporated in the bone renewal process and thus completely transformed into endogenous bone.

The various calcium phosphate apatites are derivatives of hydroxyapatite. In spite of the uniform apatite crystal structure the term apatite comprises a wide band of substances, the physiological properties of which are determined by the composition, the positions of the ions and the system conditions. Corresponding to formula III the apatite according to this invention is a well defined calcium phosphate apatite having carbonate and alkali portions, all ions being integrated in the crystal lattice at defined position and in defined quantitative ranges.

Scientific literature mentions a lot of apatite products suggested for implant purposes. They include apatites also containing carbonate ions, however, these products are usually obtained at elevated temperatures. In the case of these apatites, the carbonate ions are positioned at the hydroxy positions of the apatite lattice because of chemical reaction mechanism of the production conditions. Such apatites differ chemically and crystallographically and, above all, regarding their biological behavior considerably from the apatite according to this invention. The carbonate ions of the apatite according to this invention (as in the bone mineral) are positioned exclusively at the phosphate positions of the apatite lattice.

The carbonate and alkali containing apatite according to this invention, as is represented by formula III, only results at lower temperatures; it is not thermostable. Decarboxylation starts at 400° C. From 900° C. on, this material does not have any carbonate ions any more.

According to this invention it has been found that the presence of alkali ions at the corresponding lattice position of the apatite (as in the bone mineral) is also of major importance for the bioactivity of the apatite. In connection with the development of the apatite according to this invention the inventors succeeded in clarifying the incorporation mechanism for alkali ions in the apatite lattice of the bone mineral for the first time (completed doctoral thesis by the co-inventor Dipl.-Chem. E. Wendler, paper under print).

Only by the discovery that sodium and carbonate ions may be incorporated into the apatite lattice independent of each other has it become possible to carry out doping with these ions selectively within the phase existence room where the alkali carbonate apatites exist.

Thus, it is possible to reach any composition within the physiologically relevant field of existence and therefore produce the synthetic bone replacement material according to this invention.

The following references were considered for evaluating the patentability of the subject matter of the application:

1. EP-A No. 0,104,640 (INA SEITO)

"Sintered Apatite Bodies": Sintering takes place at elevated temperatures, an alkali component is not included. Corresponding to the above statements no product can therefore be given which is similar to the subject matter of the application.

2. U.S. Pat. No. 3,922,155 (E. LEITZ)

This reference deals with a bioglass crystallized at elevated temperatures; the same applies as stated under item 1.

3. No. DE-A 2,821,354 (Kureha Kagaku Kogyo)

This reference deals with a compound material made of sintered apatite. The sintering temperature for calcium phosphate apatite is at above 1000° C., therefore the same applies as stated under item 1.

4. DE-A No. 3,038,047 (Mitsubishi)

Herein, calcium phosphate apatite is sintered at between 500° and 1350° C.; the same applies as stated under item 1.

5. FR-A No. 2,223,325 (Research Corp.)=DE No. 24 16 087

Bone replacement material made of corals=aragonite. The product described is made of hydroxyapatite having substituted carbonate ions, it is also represented like this in the formulas. If, in contrast to the description, the carbonate ions should be incorporated into the crystal lattice, they are at the phosphate and hydroxy positions. The carbonate content and its position in the lattice cannot be controlled in this process. For this reason alone, the product of this process differs chemically and physiologically from the subject matter of the invention. The alkali component in the apatite lattice is not realized in this product.

6. EP-A No. 0,016.906 (MERCK)

Implant material from acrylate and tricalcium phosphate (TCP). Overlap with the subject matter of the invention only exist with regards to the use thereof.

7. EP-A No. 0,058,867 (Mundipharma)

This reference deals with a tricalcium phosphate product; the same applies as is stated under item 6.

8. EP-A No. 0,120,689 (Advance Kaihatsu Kenkjuko)

This reference sets forth a ceramic element made of calcium phosphates. On page 4, lines 9 to 20, a possible material variant with $CO_3$ ions at the hydroxy position is mentioned. Sintering takes place at elevated temperatures, so that the same applies as is stated under item 1.

9. U.S. Pat. No. 4,481,175 (Mitsui Toasu Chemicals, Inc.) "Process for preparing apatite"

This reference describes a process to produce hydroxyapatite by means of wet chemical tests. Page 7 states that, in the case of a precipitation product, carbonate radicals were ascertained in the hydroxyapatite upon investigation in the infrared absorption spectrum. On page 8, claim 7, a calcium phosphate apatite with carbonate radical is claimed.

In the production method described, it is not possible to control the amount of carbonate incorporation into the crystal lattice of the apatite. There is nothing stated about the position of the $CO_3$ in the lattice. An alkali component in the apatite lattice is not mentioned. The products described are therefore not comparable with the subject matter of the application.

10. DE No. 2,840,064, C2 (Scheicher, the same applicant)

"A process for the production of bone-contact layers" This reference describes the production of hydroxyapatite by calcining bones. Since the calcining process takes place at between 900° and 1100° C., the carbonate and alkali portions bonded in the starting material (bone) have escaped from the lattice; the same applies as is stated under item 1.

11. U.S. Pat. No. 3,929,971 (Della M. Roy)

"Porous Biomaterials"

This patent specification shows a large variety of possibilities to produce calcium phosphate compounds such as calcium phosphate, calcite aragonite, tricalcium phosphate and hydroxyapatite partially with carbonate portions by means of wet chemical tests and/or hydrothermally. The products are only characterized according to their chemical compositions but not according to their structures. In the given formulas the carbonate ions are represented as if they were substituted and not integrated in the crystal lattice. The possible integration of carbonate ions in the crystal lattice, however, is taken into consideration on page 15, line 25. Accurate doping and positioning of carbonate ions is not possible with this process. The alkali component is not included.

The essential features of this subject matter of the application are accurate doping and positioning of the carbonate and alkali ions; the published products described do thus not suggest the subject matter of this invention.

In the past few years, efforts have been made to investigate the crystalline structure of the bone mineral. Up to now, opinions about this subject are divided. The analytic composition of the bone mineral has long been known but up to now it had not been known how the individual ion building blocks are incorporated into the crystal lattice; this applies especially to the alkali ions and their importance for bone physiology. In the field of medicine, the opinion prevails even nowadays that the bone mineral is mainly hydroxyapatite having foreign ion portions not detailed crystallographically. By the papers of the co-inventor, Dipl.-Chem. E. Wendler (doctoral thesis in 1987 under print), the crystal lattice of the bone apatite, especially the incorporation mechanism for alkali ions and the importance of positioning the $CO_3$ ions, could be clarified for the first time. Discovering the physiologically relevant (narrowly limited) phase existence range within the possible phase existence room of alkali containing carbonate apatites is of essential importance in this connection. Only with this knowledge was it possible to develop the synthetic bone replacement material according to this invention and to adapt the substance to the properties of the bone mineral by selected doping of the foreign ions, such as, e.g., sodium and $CO_3$. The physiological alkali and carbonate containing apatite is not a pure substance but comprises (starting from the structure of the hydroxyapatite, in which all stoichiometric factors with respect to the foreign ions equal 0) a limited range of mixed crystals. The solubility in the biological milieu markedly increases with increasing carbonate and increasing alkali ion contents.

Figure 8:
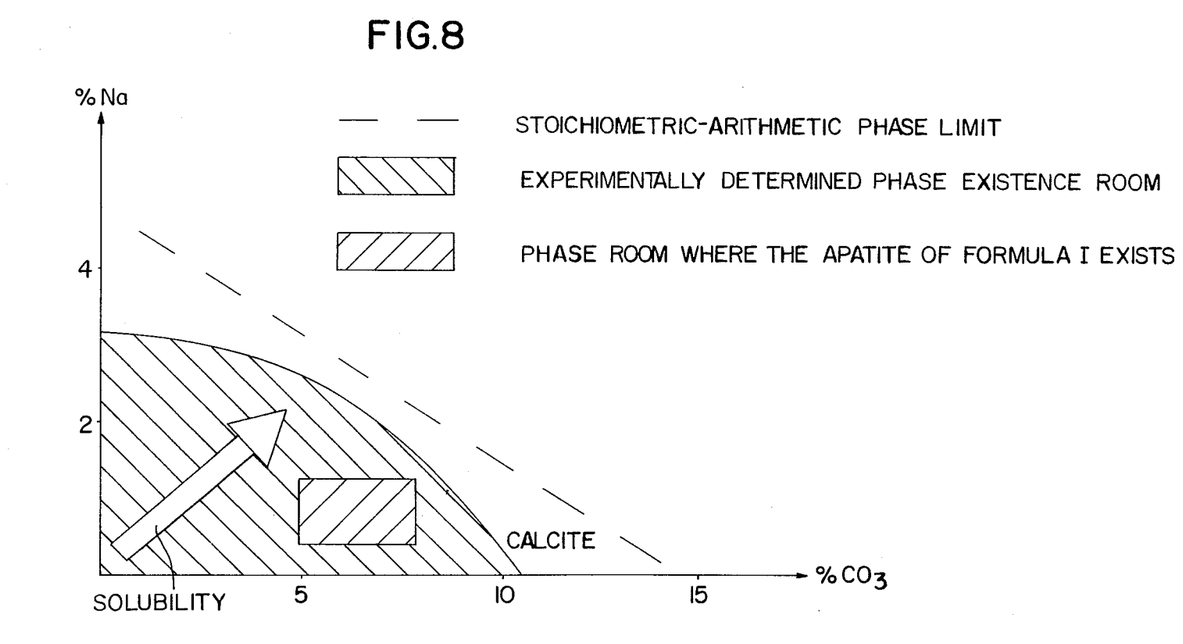
FIG. 8 is a phase existance diagram for alkali and carbonate-containing apatite.

FIG. 8 shows the chemically possible phase existence range.

The special object of the invention consists in (1.) discovering the physiologically relevant composition range of the apatite and the lattice positions of the ions essential for the physiological behavior of the mineral; (2.) developing production processes with which an implant material can be produced, which has a solubility behavior and physiological properties adapted to those of the bone, so that, on the one hand, no rejection reaction occurs and, on the other hand, resorption and dissolution, respectively, exceeding ordinary remodelling of the bone do not occur. Only by the processes according to this invention is it possible to place the relevant ions selectively in the desired amounts at the desired lattice position. This additionally renders possible the adaptation of the solubility (transformation) behavior in the physiological milieu to the requirements of the implant purpose by varying the ion doping within the physiological range.

Regarding the many references dealing with the composition of the bone mineral, two publications considered to be relevant in this connection are discussed below:

1. R. Z. LeGeros, O. R. Trautz, J. P. LeGeros, E. Klein and W. P. Shirra, "Apatite Crystallites: Effects of Carbonate on Morphology", Science, Mar. 17, 1967, pages 1409 to 1411.

As early as in 1967 alkali and carbonate containing apatites are mentioned herein. It can be taken from these statements that the incorporation of carbonate ions influences the crystallization of the apatite thereby weakening the crystal structure and increasing the solubility; this is assumed to be the cause of caries (page 1410 and 1411, left-hand column, line 6). Regarding the positioning and doping of the alkali and carbonate ions only assumptions are made. The applicants provided a carbonate containing apatite of a composition corresponding to the claims, which does not have these disadvantages.

F. C. M. Driessens, "Formation and Stability of Calcium Phosphate in Relation to the Phase Composition of the Mineral in Calcified Tissues", in K. de Groot, editor, "Bioceramics of Calcium Phosphate", CRC-Press, INC., Boca Raton, Fla., 1983.

This reference deals in detail with bone implant materials. Various calcium phosphates are described and discussed, in which other ions are additionally integrated in the hydroxyapatite structure. Especially page 5 indicates carbonate containing phosphates which, however, differ from the calcium phosphates according to this invention. This also applies to the statements made on pages 6 and 7, especially to formulas 7 and 8. These calcium and carbonate containing apatites are not suited for the present invention. Page 15 also indicates numerous apatites. None of these apatites corresponds to an apatite defined according to this invention with respect to its composition and the positioning and quantitative ranges of the ions in the lattice positions. On page 16 it is stated that combinations of apatites are to be tested to discover apatite substances corresponding to the natural bone material. However, no indications can be found as to how this can be achieved but only that exogenous substances are to be avoided. Because of the large number of possible apatite compounds and production possibilities, as can already be seen from the many patent specifications mentioned, it would actually be impossible to synthesize the substance according to this invention without being familiar with the results of the basic research conducted by the inventors.

The carbonate apatites indicated in the two references either contain the entire (hypothetical) phase range or only relate to the composition range of the abscissa of the graph, FIG. 8, which shows the correlations of the subject matter of the invention.

Summarizing it may be stated that the incorporation mechanism of the physiologically relevant foreign ions into the structure of the bone mineral had not been known. Only by clarifying these connections has it become possible to adapt the physiological behavior of the apatites purposefully to the properties of the bone mineral via the selective incorporation of foreign ions at the corresponding positions of the apatite lattice.

ANIMAL EXPERIMENT

Animal experiments were carried out with fluorescence labelling and subsequent histomorphological evaluation to make a comparison between the apatite materials according to this invention and the conventional hydroxyapatites. The results showed that the bone repair in the boundaries of the bone defect starts earlier and that the granular implant material is infiltrated by the healthy bone more rapidly for the apatite materials of the invention than is the case for the comparative materials. Signs of irritation which could be recognized by the occurrence of giant cells could not be observed. The animal experiments were conducted by a major international pharmaceutical company selling hydroxyapatite preparations for implantation purposes. The evaluation was made by an independent histomorphological institute: "Institut der Histomorphologischen Arbeitsgruppe" Dr. med. Dr. med. habil. K. Draenert, Gabriel-Marx-Straβ3, 8000 Munich 90, FRG. The institute evaluating the data was not familiar with the compositions of the preparations.

It can be concluded therefrom that, due to the chemical composition approximated to the mineral of the bone and the crystal structure of the material according to the invention, immediate bidirectional ion exchange and immediate mutual epitoxic growing onto the apatite crystals may take place, while in the case of the hydroxyapatite implants initially the surface of the crystallites has to be adapted in vivo to the crystal structure of the bone apatite by ion exchange. Because of these properties of the implant material according to this invention osteointegration of the implant material takes place without delay and irritation. A gain of time in the osteointegration of about 4 to 8 days is obtained by the implant material according to this invention.

The $MeCO_3$ apatite containing material may be produced, e.g., according to one of the following processes:

1. A hydroxyapatite masked on its surface with $MeCO_3$ apatite can be obtained from hydroxyapatite in carbonate containing aqueous suspensions by ion exchange.

This entails the use of suspensions of hydroxyapatite powder which is synthetic and/or has been obtained from calcined bone. The rate of carbonatization increases with the concentration of carbonate. The process is thus preferably carried out in solutions with a high carbonate content, for example at reaction temperatures of 20° C. The carbonate is preferably introduced into the solution in the form of the potassium and/or sodium salts (as carbonate or bicarbonate). Thus, the apatites may also be doped with Na and/or K contents thereby largely corresponding to the natural bone mineral.

The time required for 90 % of the saturation incorporation with carbonate ions is about 3 days (1m $Na_2CO_3$ solution, 20° C., Asp=33qm/g) (E. Wendler, 1987).

The starting material which is preferably used for obtaining this material masked with $MeCO_3$ apatite only on its surface is highly microcrystalline hydroxyapatite having a high specific surface, preferably microcrystalline synthetic hydroxyapatite or hydroxyapatite made from animal material, such as is obtained by, for example, the process described in German Patent Specification 2,840,064.

When these starting materials are used there is always a core of hydroxyapatite which will remain. In general, crystals in the form of powder particles with an outer layer of $MeCO_3$ apatite which is only about 0.5 to 2 nm thick, and with remaining cores of hydroxyapatite, are obtained. The product obtained in this process is particularly preferred according to the invention for bone-contact layers, in which the coating or the molded body may not be absorbed.

2. Homogenous $MeCO_3$ apatite crystals having accurate doping of the alkali and carbonate ions may be precipitated directly from calcium-phosphate-carbonate solutions. This entails addition of calcium, for example in the form of its nitrate, to boiling aqueous solutions containing carbonate and phosphate with the desired carbonate/phosphate ratio. The carbonate/phosphate ratio in the solution must be higher than that desired in the crystal. The highest possible ratio of 0.25 in the crystal is obtained with 2:1 ratio in the solution. The concentration is 0.05 to 0.2 molar.

The calcium salt is preferably added dropwise, for example an aqueous solution of calcium nitrate being added dropwise. The carbonate and the phosphate are preferably introduced into the initial solution in the form of their potassium and/or sodium salts. In order to keep the effect of hydrogen phosphate ions at a low level, the reaction should be carried out in the strongly alkaline range, for example at a pH in the range of from 12 to 14, preferably at pH 13.

After the addition of the calcium salt solution, the solution is allowed to stand at 20° C., preferably at 80° to 100° C., for some hours for the precipitation. The resulting $MeCO_3$ apatite crystals are then filtered off, washed with distilled water and dried in air.

The product obtained in this process is preferred according to the invention for the filling of bone defects, whereby the filler material is to be transformed completely to native bone.

3. Homogenous $MeCO_3$ apatite crystals may be prepared according to the following processes:

Analytically pure calcium carbonate powder is mixed with a correspondingly doped $KH_2PO_4+KOH$ and/or $NaH_2PO_4+NaOH$ solution for several days and stirred at about 90° C. for several days, preferably for about 100 hours. After cooling and sedimentation it is washed in Agua bidest several times and then dried. The $MeCO_3$ apatite crystals according to the invention are obtained. The doping of the alkali ions is controlled by the composition of the solution.

4. Production of microporous or homogenous $MeCO_3$ apatite articles or granules:

A workpiece made of bioinert material, which is constantly heated to between 30° and 250° C., is repeatedly immersed in a concentrated calcium hydroxide solution $(Ca(OH)_2)$ and/or a calcium hydrocarbonate solution $(Ca(HCO_3)_2)$ briefly (for 5 to 10 seconds) and then taken out of the solution until the water is completely evaporated. By this the $Ca(OH)_2$ dries in layers and simultaneously the crystals intergrow with one another. This process is repeated until enough material is attached. Then, the resulting solid is exposed to a saturated atmosphere of steam and carbon dioxide at about 90° C. for several days. As a result, the $Ca(OH)_2$ is reacted to form calcium carbonate $CaCO_3$. The retention time depends on the thickness and density of the material. Preferably, the drying process is carried out in a carbon dioxide atmosphere, whereby the reaction to $CaCO_3$ takes place at the same time. Then, the material is further treated as is described under item 3. The resulting material is separated from the heated body and processed to give molded parts or granules.

5. In the same way as is described under item 4, implant articles made from biocompatible material can be uniformly coated with the $MeCO_3$ apatite according to the invention. In this connection, it is often expedient to add most fine biocompatible fibers, such as aluminum oxide $(Al_2O_3)$, silicon carbide (SiC), hydoxyapatite, preferably in the form of whiskers to compact the coating material of the $Ca(OH)_2$ solution.

In this case, the fibers must be held suspended in the liquid by pulsation, vibration or turbulences. The homogeneity of the $MeCO_3$ apatites produced as indicated under items 4 and 5 can be controlled by the temperature during the drying step; the lower the temperature and the slower the growing on process, the more homogenous the coating is. Very rapid growing on and a high degree of porosity of the material are achieved when metallic calcium is added to the $Ca(OH)_2$ solution, so that there is an excess of $Ca(OH)_2$ formed always newly.

6. The $MeCO_3$ apatites described under items 2 to 5 may be recrystallized by calcining at 900° C by releasing the $CO_2$ and alkali portions to give the hydroxyapatite and then, as is described under item 1, masked on the surface with $MeCO_3$ apatite or by renewed coating, as is described under items 4 and 5, coated with homogenous $MeCO_3$ apatite. This measure is especially advantageous for implants and implant coatings which shall not be absorbed.

7. To increase the absorption resistance of the $MeCO_3$ apatite according to the invention fluoride ions can be incorporated in its crystal lattice in exchange for OH ions at the OH positions. The halogen ions are incorporated by introducing the $MeCO_3$ product in corresponding halide salt solutions. For incorporating fluoride ions the product is immersed, e.g., in a 1 molar sodium fluoride solution at 20° C. and stirred. The exchange rate of fluoride ions to hydroxy ions depends on the pH value of the solution, its concentration and the time. The doping of the fluoride ions are hereby controlled. After this treatment, the product has to be washed several times in Agua bidest.

DETAILED DESCRIPTION OF THE DRAWINGS

The invention is illustrated in detail by means of the drawings which are attached.

Figure 1:
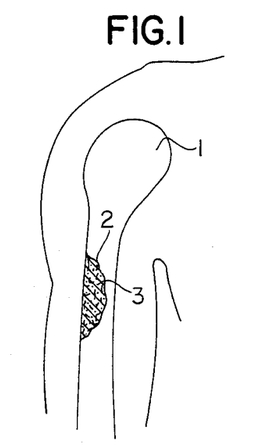
FIG. 1 illustrates an arm bone having a defect therein which is filled with the material according to the invention.

FIG. 1 shows a bone 1 with a bone defect 2 which has resulted from, for example, an operation for the removal of a malignant tumor. The material 3 according to the invention is packed into the cavity 2 and becomes knitted in there. After the knitting in, which takes place virtually without signs of irritation, the bone can again be used and subjected to stress as normal, without the patient experiencing pain. It is also possible to fill huge defects, for example cavities with a volume of 200 to 800 cm³, by the process shown in FIG. 1.

Figure 2A:
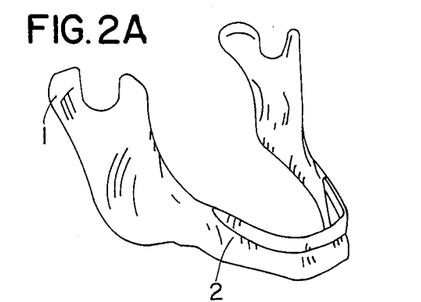
FIGS. 2a-2c illustrate a jaw bone treated with the material according to the invention.
Figure 2B:
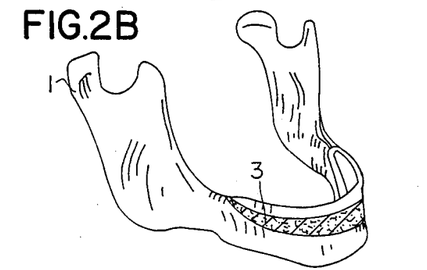
Figure 2C:
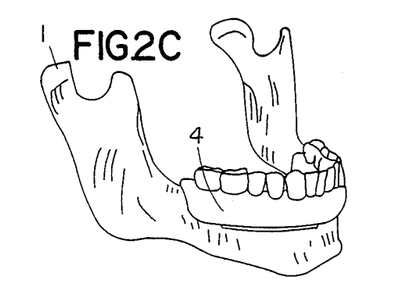

Another possible use of the $MeCO_3$ apatite is reproduced in FIGS. 2A, 2B, and 2C. As shown in FIGS. 2A-2C, the external shape of a bone can be modified by, for example, cutting through a toothless jaw bone which has undergone resorption, and providing an interlayer of $MeCO_3$ apatite by the so-called sandwich process. In FIGS. 2A-2C, 1 the bone, 2 is the cutting line 3 is the material according to the invention and 4 is a complete denture in place.

Figure 3A:
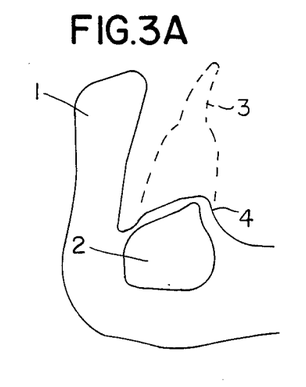
FIGS. 3a-3b illustrate a sagittal section through the lower jaw in the region of the front teeth.
Figure 3B:
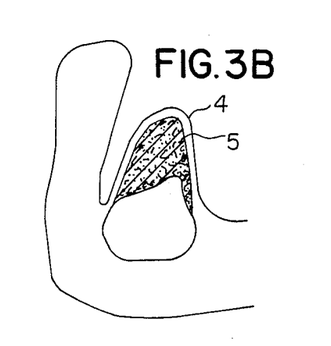

The embodiment reproduced in FIGS. 3A and 3B serve for, in particular, building up bone, for example where the ridge of the jaw has undergone resorption, or in plastic surgery to shape facial bones after injury or tumor removal. In such cases it is possible to detach the periosteum, form an envelope fill the $MeCO_3$ apatite into the envelope which has been formed, and thus build up the bone.

FIGS. 3A and 3B show a sagittal section through the lower jaw in the region of the front teeth, 1 being the lower lip, 2 being the bone, 3 being the original contour of the jaw with tooth, 4 being the mucous membrane, and 5 being the material according to the invention.

Figure 4A:
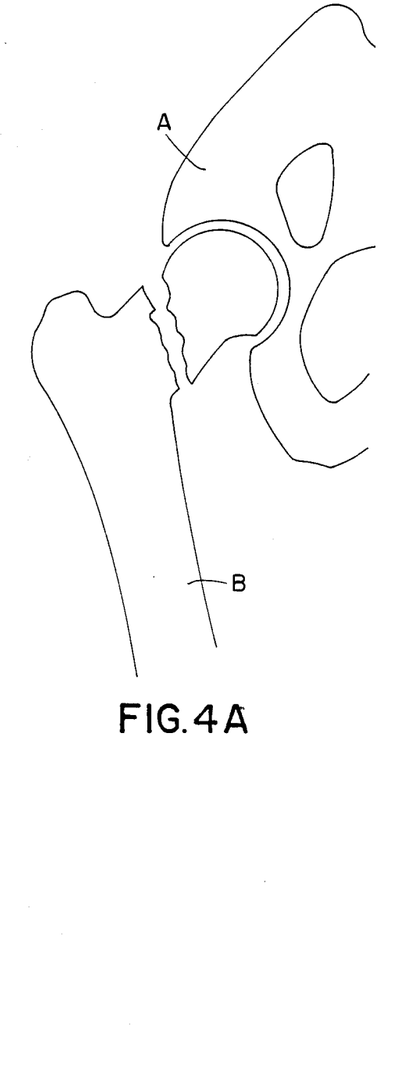
FIGS. 4a-4b illustrate implantation of a hip joint prosthesis with the material according to the invention.
Figure 4B:
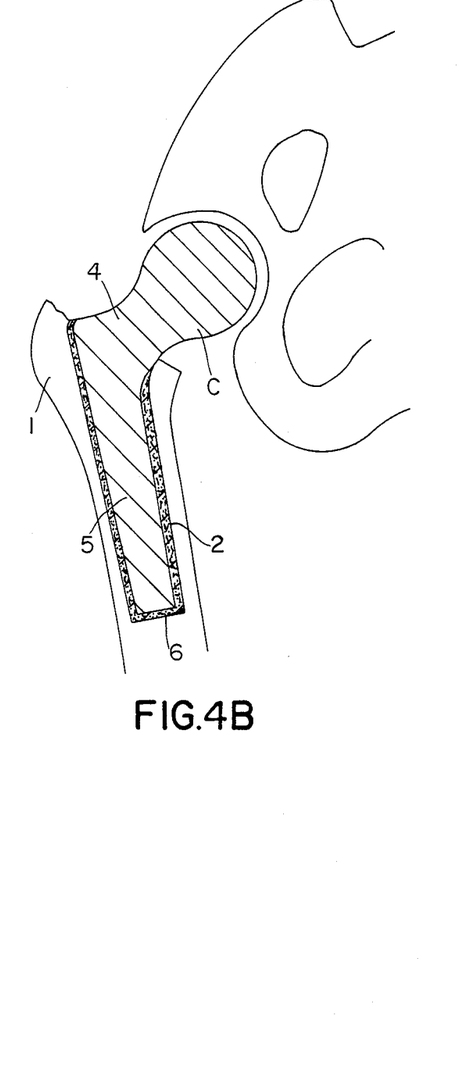

As shown in FIGS. 4B and 4B it is also possible to insert an article 4 for implantation into the bone 1 which has a cavity 2. The article 4 for implantation comprises a core 5 and a bone-contact layer 6 composed of $MeCO_3$ apatite. The article 4 for implantation has a surface coating of MeCO$_3$ apatite. However, it is also possible for the article 4 for implantation to be composed entirely of MeCO$_3$ apatite.

The use of MeCO$_3$ apatite according to the invention is illustrated in detail by the hipjoint prosthesis shown in FIGS. 4A and 4B. A fracture of the neck of the femur with a fracture line which has an unfavorable course (hip bone A, femur B) is necessarily managed surgically with an artificial articular head C. The connection to the substrate bone is effected using an implant which is coated with MeCO$_3$ apatite according to the present invention.

With an embodiment of this type, there is a rapid, rigid and durable union set up between the prosthesis and the bone, and this is crucial for the success of the operation. Hipjoint operations are very stressful for patients. The use of bone cement to fix the implant in place, which is customary at present, is in need of improvement and, as already mentioned, nowadays one quarter of all hipjoint operations of this type are repeat operations which have become necessary because of loosening of the endoprosthesis. The shortening of the period of irritation, which has surprisingly been found, leads to the expectation that there will be a reduction in the frequency of second operations of this type.

Figure 5:
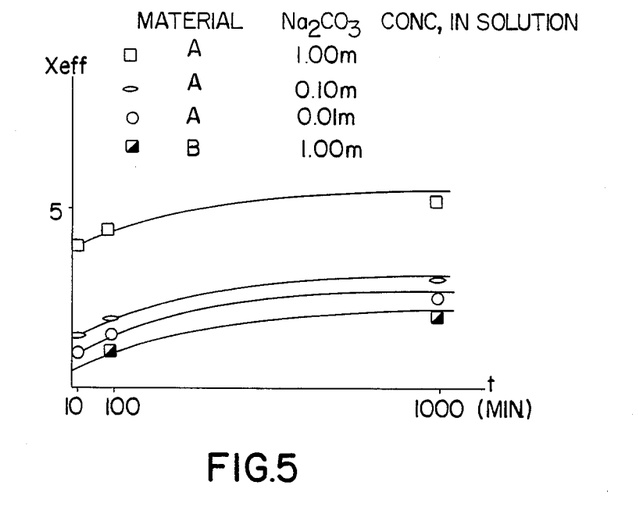
FIG. 5 is a graph of the incorporation of sodium and carbon ions as a function of time for solutions of different concentrations.
Figure 6:
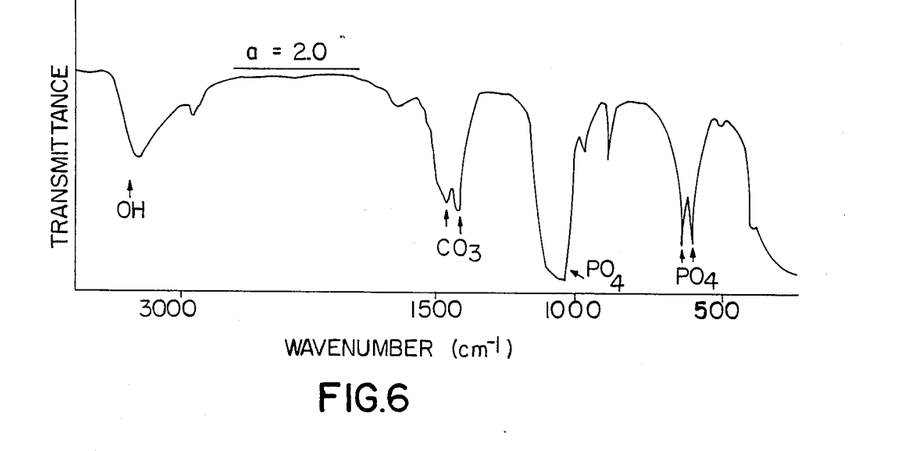
FIG. 6 illustrates an IR spectrum of a carbonate-apatite product.

FIG. 5 reproduces the time course of the incorporation of sodium and carbonate ions in hydroxyapatite as a function of the concentration of the solution and the specific surface area of the apatite powder. FIG. 6 reproduces the IR spectrum of the carbonate-apatite product obtained as in Example 3, and FIG. 7 reproduces the IR spectrum of mammalian bone.

FIG. 8 shows the chemically possible phase existence range for alkali and carbonate containing apatite. The hatched rectangle represents the physiologically relevant existence range within this system. It can be seen that only a very narrow composition range is in consideration for use as an implant material.

The insertion of the agent according to the invention and the use of the MeCO$_3$ apatite are illustrated in detail below.

1. Use of MeCO$_3$ apatite for filling defects in bone and teeth and for building up bone.

1.1 Loose filling

Homogenous MeCO$_3$ apatite is used as a loose filling in cases where there is no necessity for the filling to have mechanical strength after it has been introduced, or for it to form a primary closure of the defect toward the surroundings, or where the filling is exposed to no or only slight deforming forces and is intended primarily to bring about rapid healing.

Function

The intention is that the agent temporarily occupies the defect and that living bone grows through it as rapidly as possible and subsequently breaks it down and replaces it. It is essential that ingrowth of replacement scar tissue is prevented and that the bone cells which are growing in are presented with a favorable milieu, such as adequate porosity, physiological composition and solid particles which resemble bone mineral and which merely need to be connected by newly deposited bone mineral in order to bridge over the defect with bony material.

In this way the restoration of bone which can be stressed normally is, depending on the position and size of the defect, either made possible for the very first time or dramatically shortened from years to weeks.

EXAMPLES

An example of this is the filling of minor defects where the remaining bone is able to bear loads or is held by other measures, such as use of a plate, or a plaster cast, such as cysts in the jaw bone, tooth socket after extraction, periodontal bone defects, foci of suppuration in bone which have been cleared out (osteomyelitis), tumor bed in bone, defects caused by comminuted fracture (surgical union of the pieces of bone by plate osteosynthesis) or building up bone by the sandwich technique, as is shown in FIG. 2 for example.

Homogenous MeCO$_3$ apatite powder or granules with a particle size from about 0.1 to 2 mm are used for this purpose. The agent can contain as an additive aqueous media, such as physiological buffers and salt solutions or autologous blood, and possibly relatively soft absorbable binders, such as polysaccharides or polypeptides. The amount added must be enough to obtain a gas-free mixture, and a slight excess may be desirable to improve the ease of processing. The MeCO$_3$ apatite has, for example, a computed density of 3.4 g/cm$^3$, the bulk density depending on the shape and size of the particles and ranging from 1.0 g/cm$^3$ to 3.0 g/cm$^3$ (density of the additives around 1.0 g/cm$^3$).

An agent for this application contains, for example 30 to 80% by weight of MeCO$_3$ apatite and 70 to 20% by weight of additives of the type detailed above.

Examples of other suitable additives in small amounts are infection inhibiting, blood flow promoting and bone growth promoting medicaments, hormones and chemicals.

For the actual use, the agent can be packed sterile in injectors for smaller amounts, otherwise in screw-top bottles, cans, etc. For use with blood or additives, it is also possible to pack the agent and the additive separately in solid form, and they are then mixed together on use.

1.2 Solid fillings

Solid fillings are used in cases where the intention is that the agent, after introduction or application, solidifies to a rigid mass which can be subjected to mechanical stress and has a stable shape, forms a primary leakproof closure of the defect or adheres strongly to the bone.

Function

The intention is that the agent immediately fills the defect solidly and flush with the margins, and rapidly fuses with the bone and that, over the course of time, living bone slowly grows through it and partially replaces it. Depending on the area of use, it is important for there to be a leakproof closure which prevents the penetration of microbes, a frictional connection to the bone together with the ability to withstand mechanical stress, or a stable shape and rigid adhesion. The binder forms a stable matrix in which the MeCO$_3$ apatite particles are held fixed, and it adheres to the bone after setting. The MeCO$_3$ apatite particles on the surface allow growth onto the filling in the bone, and living bone grows through the material when the porosity is sufficient, it being acceptable if a matrix of binder which cannot be absorbed is left behind.

The agent makes it possible to carry out functional replacement, which can be immediately subjected to stress, of parts of bone, and this is slowly replaced, or at least permeated, by living bone.

EXAMPLES

Examples of the use of solid fillings are the filling of large bone defects resulting from infection, injury or tumors, where the remaining bone is no longer able to withstand stress adequately, bonding of the fragments from comminuted fractures, building up free-standing bone (see FIG. 3) and filling of the nerve canal in teeth.

Composition of the agent

When intended for this use, a powder or granules of $MeCO_3$ apatite (fine powder for tooth fillings, medium particle sizes 0.1 mm for bone defects and granules around 1 mm for building up bone) is used. Suitable additives are non-toxic binders which harden at body temperature with evolution of little heat, such as acrylates, polyesters, cements, etc., and gelling agents may also be suitable where the stress is very low. Depending on the binder and particle size, the content of $MeCO_3$ apatite can be 10 to 50% by weight, thus, the resulting figures depending on the specific gravity of the binder are 5 to 80% by weight of $MeCO_3$ apatite and 95 to 20% by weight of binder. Addition of 10 to 30% by weight of calcium hydroxide is suitable for nerve cappings on teeth.

The agent can be marketed in the form of a two-component agent. One component is composed of $MeCO_3$ apatite and the second component is composed of the binder. However, it is also possible to manufacture finished mixtures of $MeCO_3$ apatite and binder, which optionally contain further additives, and to market these as described in 1.1. The additives which can be used are the above-mentioned additives as well as additional solvents and/or blowing agents to increase the porosity.

2. Coating and manufacture of implants with $MeCO_3$ apatite 2.1 Bone-contact layers If the intention is to provide a bone implant which combines the good mechanical properties of biocompatible materials with the ideal bioactive contact properties of $MeCO_3$ apatite it is worthwhile to apply a coating.

Function

The purpose of the bone-contact layer on the implant is to offer to the substrate bone a surface which resembles bone as closely as possible, so that the implant is not regarded as a foreign body and is incorporated like a fractured piece of bone rigidly in the mineral framework of the bone. The important factor in this is not the thickness of the contact layer but only the chemical composition of the outermost layer of molecules. Another important factor is rigid adhesion to the implant core. A contact layer of this type makes it possible for a frictional connection between the bone and implant to form rapidly, and thus the settling times are shortened and loosening becomes less probable.

EXAMPLES

Every type of bone implant, including tooth root implants, can be provided with bone-contact layers. It is possible to press a dry $MeCO_3$ apatite powder onto implants made of other materials.

Furthermore, it is possible to apply to implants mixtures of $MeCO_3$ apatite with the additives described under 1.2. It is also possible to coat the article for implantation first with a layer of pure binder and then with a mixture as described above under 1.2. To increase the $MeCO_3$ apatite content on the surface it is possible for $MeCO_3$ apatite to be scattered onto the coated implant before the binder has hardened, or for the implant to be rolled in $MeCO_3$ apatite.

Articles for implantation which are made from other materials can also be coated with the agent according to the invention by so-called sputtering or cathode-atomization processes, the plasma spray process and isostatic pressing. A coating of this type can also be effected by ion-implantation processes. A target of the purest possible $MeCO_3$ apatite is used for sputtering. For pressing, the layer is first applied as a mixture of soft binder, for example agarose, and fine $MeCO_3$ apatite powder or aqueous solutions.

Another possibility for the manufacture of implants coated with $MeCO_3$ apatites is the chemical conversion of hydroxyapatite into $MeCO_3$ apatite as described above. Implants which have been produced from hydroxyapatite or materials containing hydroxyapatite or are coated with them are surface-coated with $MeCO_3$ apatite by the wet chemical process which has been described.

The finished, coated implants can be marketed commercially.

2.2 Manufacture of implants composed of materials containing $MeCO_3$ apatite

If the mechanical requirements of a bone implant are not very exacting or if the intention is for living bone grow entirely through it or replaces it over the course of time, the implant can be manufactured entirely of $MeCO_3$ apatite or material containing $MeCO_3$ apatite.

Function

As 2.1, in addition it is possible, by appropriate choice of the binder and/or the porosity, for living bone entirely or partially to grow through or replace the implant.

EXAMPLES

Every type of bone implant, including tooth root implants, as long as the resistance to mechanical stress is sufficient.

Implants of this type are manufactured from $MeCO_3$ apatite with binder. The composition of the agent according to the invention resembles that described above under 1.2. Fibers, wires, fabric, meshworks or networks can be introduced for reinforcing. These can be composed of, for example, metals, such as noble metals, steels or titanium, or of synthetic and natural fibers, for example carbon fibers, glass fibers, whiskers and natural and synthetic yarns, or fibers obtained from animal tissues. The implants are manufactured in appropriate negative molds, and this is followed by, where appropriate, consolidation by application of pressure.

The examples which follow illustrate the invention.

EXAMPLE 1

100 g of powdered hydroxyapatite are prepared from animal bone by the process described in German Offenlegungsschrift No. 2,840,064 and are stirred in 1000 ml of 1 molar sodium carbonate solution at 20° C. in a beaker for 72 hours. The sediment is then removed by filtration in a customary manner, and is washed once in 0.5 l of 1N hydrochloric acid and three times in distilled water, and is removed by filtration.

Finally, the filter cake is dried in a hot-air oven for 60 minutes. As FIG. 5 shows, 80% saturation is reached even at room temperature after 100 minutes in a 1 molar solution. The resulting whitish powder is composed of finely dispersed $MeCO_3$ containing apatite crystals which are used as starting material for the agent and the bone-contact layers.

EXAMPLE 2

500 g of hydroxyapatite granules (Osbonite ®, Calcitite ®) are added to a vessel which contains 2 l of 1 molar potassium carbonate solution at room temperature and through which carbon dioxide gas is blown from below. The gas which is blown in brings about continuous agitation of the granules and keeps the solution saturated with potassium and carbonate ions.

The granules are removed after 60 minutes and are washed and dried as described in Example 1. The resulting granules comprise particles whose outer layers have been converted into $MeCO_3$ apatite, and they are used as base material for the agent.

EXAMPLE 3

1 mole of potassium phosphate and 2 moles of potassium carbonate are dissolved in 2 l of boiling distilled water, and the pH is adjusted to 13.0 with potassium hydroxide. 2 moles of calcium nitrate are added to the solution and, while stirring continuously, the mixture is boiled under reflux for 60 minutes. Thereafter, the solution is allowed to stand at 60° C. for 24 hours, and then the precipitate is filtered off, washed several times with distilled water and dried in a hot-air oven at 120° C. for 4 hours.

Figure 7:
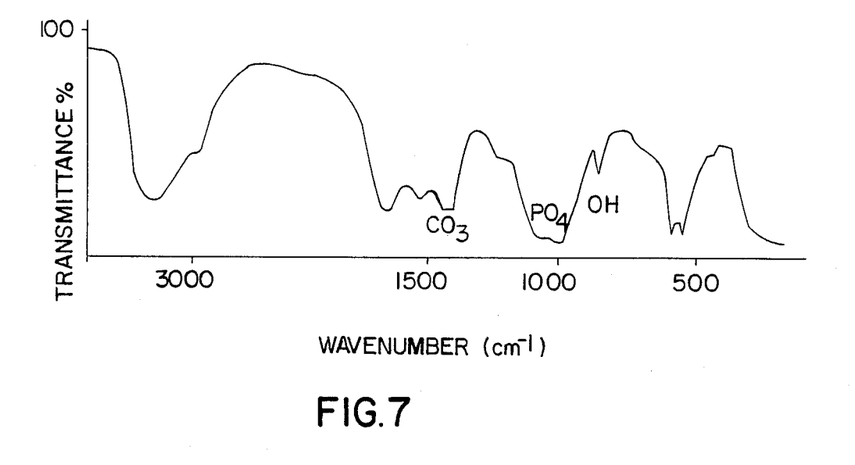
FIG. 7 illustrates an IR spectrum of mammalian bone.

FIG. 6 shows the infrared spectrum of the product which, as comparison with the spectrum of mammalian bone in FIG. 7 shows, is chemically very similar to bone. About 250 g of pure $MeCO_3$ apatite crystals are obtained, and these are used as the starting material for the agent and the bone-contact layers.

EXAMPLE 4

1 mole of potassium phosphate and 0.2 mole of sodium carbonate are dissolved in 2 l of boiling bidistilled water, and then the process is continued as in Example 3. The product obtained is about 250 g $MeCO_3$ containing apatite crystals whose sodium content is also very similar to that of bone mineral and which are suitable as starting material for the agent and the contact coating.

EXAMPLE 5

100 g of $MeCO_3$ containing apatite or $MeCO_3$ apatite prepared as in Example 1 or by another process are stirred into 100 ml of a 3% agarose solution. The subsequent processing and use are carried out as described in detail in German Offenlegungsschrift No. 2,657,370.

A pasty material is obtained, and this is suitable for the filling of bone defects.

EXAMPLE 6

The granules produced as in Example 2 are mixed with an approximately equal volume of physiological sodium chloride solution so that the presence of supernatant liquid is just avoided. This mixture is introduced into injectors or other vessels which are closed air-tight and packed sterile.

The agent thus obtained can be directly injected or packed into bone defects during an operation.

EXAMPLE 7

The powder prepared as in Example 4 is mixed with equal parts by weight of bone cement polymer, and the mixture is packed into containers. The liquid monomer is not added until used in accordance with the instructions of the cement manufacture.

The mixture, which is initially pasty, can be introduced into defects in bone or teeth and forms, after a short time, a hard material capable of load-bearing.

EXAMPLE 8

A bone implant is provided with a hydroxyapatite-containing ceramic coating by the process described in German Offenlegungsschrift No. 2,840,064. The implant is then left in a 1 molar sodium carbonate solution at 20° C. for 72 hours.

After this treatment the contact layer is composed of $MeCO_3$ containing apatite.

EXAMPLE 9

A tooth-root implant made of alumina is rotated about its long axis in a sputtering apparatus (cathode atomization apparatus) to coat it with particles which have been atomized from a $MeCO_3$ apatite target. Owing to the extremely high speed at impact, the particles penetrate into the surface of the implant and adhere strongly to it. An overall coating is attained after 8 hours.

As the result of the ESCA investigation (electron spectroscopy for chemical analysis) shows, aluminum atoms are no longer detectable on the surface of an alumina article coated in this manner.

EXAMPLE 10

The enossal part of an endoprosthesis or a tooth implant is coated with $MeCO_3$ apatite by immersion as described under production processes 4 and 5. Good adhesion of the coating is obtained by previous mechanical roughening and/or a electrochemical pretreatment of the stem material in calcium hydroxide solution.

EXAMPLE 11

The stem section of a hipjoint endoprosthesis made of special steel is painted with low viscosity bone cement (methacrylate), and $MeCO_3$ containing apatite powder prepared as in Example 4 is scattered on. After the cement has set, the procedure is repeated until a sufficiently thick, overall coating is attained.

EXAMPLE 12

A mixture of 50% $MeCO_3$ apatite (from Example 3), 48.5% water and 1.5% agarose is made into a paste and heated at 100° C. Before this mixture has cooled to the gelling temperature of the agar it is packed into the negative mold for a toothroot implant. After cooling, the preformed implant is removed and dried in air at room temperature for 72 hours. The article is then highly compressed by the isostatic compression process.

The implant thus obtained can be used directly as a toothroot implant.

EXAMPLE 13

A bone tumor in the humerus is removed by surgery and the resultant cavity is filled with the material described in Example 5. The filling material can be subjected to mechanical stress and can contribute to bearing a part of the load on the bone immediately after the cement has hardened, notwithstanding the fact that living bone grows through it and replaces it over the course of time.

EXAMPLE 14

A tibial fracture is followed by osteomyelitis. The focus is opened up and, after removal of the dead bone material, the defect is packed with filling material from Example 6 which has been mixed with an antibiotic or colloidal silver, depending on the spectrum of pathogens.

EXAMPLE 15

Where the ridge of the jaw in a toothless jaw is too low and no longer provides an adequate support for a complete denture, surgery is carried out to expose the bone, cut through it in the transverse plane in the region of the front teeth, lift it and insert an interlayer of granules from Example 3, mixed with approximately an equal volume of fresh blood from the patient.

After closure of the wound, the ridge of the jaw which has thus been built up is supported with a temporary plastic splint, and the definitive dental prosthesis can be provided after 3 weeks.

EXAMPLE 16

For a fracture of the neck of the femur of an elderly patient, after the articular head has been removed and appropriate drilling has been carried out in the femur, an endoprosthesis treated as in Example 10 is inserted without cement (compare FIG. 4).

The implant can be subjected to stress immediately and it rapidly and rigidly fuses with the bone.

EXAMPLE 17

After extraction of a tooth which can no longer be preserved, the tooth socket in the jaw bone is widened with appropriate borers and an artificial tooth root, coated as described in Example 10, is implanted. After a settling period lasting some weeks, the superstructure (crown) is positioned thereon.

EXAMPLE 18

Where there is deep-seated dental caries, which extends into the nerve (pulp) of the tooth, the carious material is completely removed in the customary manner, and then the defect is filled with a paste prepared from 10% calcium hydroxide, 40% meCO$_3$ apatite prepared as in Example 5, and 50% physiological sodium chloride solution (so-called nerve capping).

EXAMPLE 19

In the case of pulp-dead tooth, the root canal is carefully cleaned out and the defect is packed with a pasty mixture of 65% PMMA plastic and 35% MeCO$_3$ apatite powder from Example 1 (so-called root filling).

We claim:

1. An agent for filling bone defects, for building up bone, for forming bone-contact layers on the replacements of bones and roots of teeth and for making independent smaller bone replacement parts or implant articles, comprising a calcium phosphate apatite having carbonate and alkali portions, all ions being definedly integrated in the crystal lattice, of the following formula:

$$Ca_{10-a-b-x}Me^{II}_aMe^{I}_b(PO_4)_{6-x}(CO_3)_x(OH)_{2-b-x}(H_2O)_w$$

wherein

Me$^I$ is a singly charged metal ion,

Me$^{II}$ is a doubly charged metal ion, a represents the number of double charged metal ions with the exception of Ca and is a value from 0 to 1.0, b represents the number of singly charged metal ions and is a value from 0.05 to 1.2, x represents the number of carbonate ions and is a value from 0.02 to 1.2, the sum b+x being a maximum of 2.0, and w represents the number of water molecules integrated in the crystal lattice and is a value from 0 to b+x wherein at least a portion of the Me$^I$ ions are alkali ions and the CO$_3$ ions are positioned at the PO$_4$ positions within the apatite lattice.

2. An agent according to claim 1, further comprising at least one compound selected from the group consisting of conventional physiologically acceptable additives and diluents of bone replacement materials.

3. An agent according to claim 2, comprising at least one compound selected from the group consisting of organic binders, inorganic binders, physiological salt solutions, medicaments and hormones as physiologically acceptable additives.

4. An agent according to claim 1, containing 1 to 100% by weight of calcium phosphate apatite of the formula.

5. The agent according to claim 1, wherein, in the calcium phosphate apatite of formula I, a portion of the hydroxy ions is exchanged for halide ions and/or a portion of the Ca$^{2+}$ ions and OH$^-$ ions is exchanged for singly charged metal ions and/or a portion of the Ca$^{2+}$ ions is exchanged for doubly charged metal ions.

6. A process for filling bone and tooth defects, for building up bone, for providing bone-contact layers, for bone replacement, or for tooth-root replacement comprising bringing into contact the affected region of bone or tooth with a material containing a calcium phosphate apatite having alkali and carbonate portions, in which all ions are definedly integrated in the crystal lattice, of the following formula:

$$Ca_{10-a-b-x}Me^{II}_aMe^{I}_b(PO_4)_{6-x}(CO_3)_x(OH)_{2-b-x}(H_2O)_w$$

wherein

Me$^I$ is a singly charged metal ion,

Mw$^{II}$ is a doubly charged metal ion, a represents the number of doubly charged metal ions with the exception of Ca and is a value from 0 to 1.0, b represents th number of singly charged metal ions and is a value from 0.05 to 1.2, x represents the number of carbonate ions and is a value from 0.2 to 1.2, the sum b+x being a maximum of 2.0, and w represents the number of water molecules integrated in the crystal lattice and is a value from 0 to b+x, wherein at least a portion of the Me$^I$ ions are alkali ions and the CO$_3$ ions are positioned at the PO$_4$ positions within the apatite lattice.

7. The process according to claim 6, wherein, in the calcium phosphate apatite of formula I, a portion of the hydroxy ions is exchanged for halide ions, and/or a portion of the Ca$^{2+}$ ions and OH$^-$ ions is exchanged for singly charged metal ions and/or a portion of the Ca$^{2+}$ ions is exchanged for doubly charged metal ions.

8. An implant article containing calcium phosphate apatite having alkali and carbonate portions, all ions being definedly integrated in the crystal lattice, wherein the apatite has the formula:

$$Ca_{10-a-b-x}Me^{II}_aMe^{I}_b(PO_4)_{6-x}(CO_3)_x(OH)_{2-b-x}(H_2O)_w$$

wherein
  $Me^I$ is a singly charged metal ion,
  $Me^{II}$ is a doubly charged metal ion,
  a represents the number of doubly charged metal ions with the exception of Ca and is a value from 0 to 1.0,
  b represents the number of singly charged metal ions and is a value from 0.05 to 1.2,
  x represents the number of carbonate ions and is a value from 0.2 to 1.2, the sum b+x being a maximum of 2.0, and
  w represents the number of water molecules integrated in the crystal lattice and is a value from 0 to b+x,
wherein at least a portion of the $Me^I$ ions are alkali ions and the $CO_3$ ions are positioned at the $PO_4$ positions within the apatite lattice.

9. The implant article according to claim 8, wherein, in the calcium phosphate apatite of formula I, a portion of the hydroxy ions is exchanged for halide ions, and/or a portion of the $Ca^{2+}$ ions and $OH^-$ is exchanged for singly charged metal ions and/or a portion of the $Ca^{2+}$ ions is exchanged for doubly charged metal ions.

10. An agent according to claim 2, containing 1 to 100% by weight of calcium phosphate apatite having carbonate and alkali portions according to the formula.

11. An agent according to claim 3, containing 1 to 100% by weight of calcium phosphate apatite having carbonate and alkali portions according to the formula.

12. An agent according to claim 2, wherein, in the calcium phosphate apatite of the formula, a portion of the hydroxy ions is exchanged for halide ions, and/or a portion of the $Ca^{2+}$ ions and OH ions is exchanged for singly charged metal ions and/or a portion of the $Ca^{2+}$ ions is exchanged for doubly charged metal ions.

13. An agent according to claim 3, wherein, in the calcium phosphate apatite of the formula, a portion of the hydroxy ions is exchanged for halide ions and/or a portion of the $Ca^{2+}$ ions and OH ions is exchanged for singly charged metal ions and/or a portion of the $Ca^{2+}$ ions is exchanged for doubly charged metal ions.

14. An agent according to claim 4, wherein, in the calcium phosphate apatite of the formula, a portion of the hydroxy ions is exchanged for halide ions, and/or a portion of the $Ca^{2+}$ ions and OH ions is exchanged for singly charged metal ions and/or a portion of the $Ca^{2+}$ ions is exchanged for doubly charged metal ions.

15. An agent according to claim 1, wherein all of said $Me^I$ are alkali ions.

16. An agent according to claim 1, wherein $Me^I$ is $Na^{30}$, $K^{30}$, $Ag^+$, the combination $Ca^{2+}+OH$ or combinations thereof.

17. An agent according to claim 1, wherein $Me^{II}$ is $Mg^{2+}$, $Pb^{2+}$, $Sr^{2+}$, $Cd^{2+}$, $Mn^{2+}$, $Ca^{2+}$ or combinations thereof.

18. An agent according to claim 1, wherein $Me^I$ is $Na^{30}$.

19. An agent according to claim 1, wherein at least a portion of said $Me^I$ ions are $K^+$ ions.

20. An agent according to claim 1, wherein F ions are incorporated into the apatite lattice at the OH positions.

21. An agent according to claim 2, wherein said agent comprises about 30-80 weight percent of said calcium phosphate apatite and about 20-70 weight percent of at least one compound of said conventional physiologically acceptable additives.

22. An implant article according to claim 8, wherein said implant article consists entirely of said calcium phosphate apatite.

23. An implant article according to claim 8, wherein said article is an endoprosthesis which is at least partially coated with said calcium phosphate apatite.

24. An implant article according to claim 8, wherein said article comprises a hydroxyapatite core with an external coating of said calcium phosphate apatite.

25. An implant article according to claim 8, wherein said article is an implant of biocompatible material with a uniform outer coating of said calcium phosphate apatite.

* * * * *

UNITED STATES PATENT AND TRADEMARK OFFICE
CERTIFICATE OF CORRECTION

PATENT NO. : 4,917,702

DATED : April 17, 1990

INVENTOR(S) : HANS SCHEICHER ET AL

It is certified that error appears in the above-identified patent and that said Letters Patent is hereby corrected as shown below:

Column 20, claim 5, lines 28-29:

reads "The agent according to claim 1, wherein, in the calcium phosphate apatite of formula I, a portion of the"

should read -- An agent according to claim 1, wherein, in the calcium phosphate apatite of the formula, a portion of the --

Column 20, claim 7, line 64:

reads "calcium phosphate apatite of formula I, a portion of the"

should read -- calcium phosphate apatite of the formula, a portion of the --

Column 21, claim 9, lines 26-27:

reads "The implant article according to claim 8, wherein, in the calcium phosphate apatite of formula I, a portion"

should read -- An implant article according to claim 8, wherein, in the calcium phosphate apatite of the formula, a portion --

UNITED STATES PATENT AND TRADEMARK OFFICE
CERTIFICATE OF CORRECTION

Page 2 of 2

PATENT NO. : 4,917,702

DATED : April 17, 1990

INVENTOR(S) : HANS SCHEICHER ET AL

It is certified that error appears in the above-identified patent and that said Letters Patent is hereby corrected as shown below:

Column 22, claim 16, line 15:

reads "$Na^{30}$, $K^{30}$, $Ag^+$, the combination $Ca^{2+}$ +OH or com-"

should read -- $Na^+$, $K^+$, $Ag^+$, the combination $Ca^{2+}$ +OH or com- --

Column 22, claim 18, line 21:

reads "$Na^{30}$."

should read -- $Na^+$. --

Signed and Sealed this

Tenth Day of September, 1991

Attest:

HARRY F. MANBECK, JR.

Attesting Officer

Commissioner of Patents and Trademarks